United States Patent [19]

Neef et al.

[11] 4,298,538
[45] Nov. 3, 1981

[54] 16-DIMETHYLAMINOMETHYLENE-3-METHOXY-1,3,5-(10)-ESTRATRIEN-17-ONE, A PROCESS FOR THE PREPARATION THEREOF AND ITS USE AS A PREPARATIVE INTERMEDIATE

[75] Inventors: Günter Neef; Ulrich Eder; Gregor Haffer; Gerhard Sauer, all of Berlin, Fed. Rep. of Germany

[73] Assignee: Schering, Aktiengesellschaft, Berlin and Bergkamen, Fed. Rep. of Germany

[21] Appl. No.: 104,949

[22] Filed: Dec. 18, 1979

[30] Foreign Application Priority Data

Dec. 22, 1978 [DE] Fed. Rep. of Germany ....... 2856578

[51] Int. Cl.$^3$ .............................................. C07J 1/00
[52] U.S. Cl. .................................................... 260/397.4
[58] Field of Search ...................................... 260/397.4

[56] References Cited

U.S. PATENT DOCUMENTS 3,091,609  5/1963  Schaub et al. ................... 260/397.4

*Primary Examiner*—Elbert L. Roberts
*Attorney, Agent, or Firm*—Millen & White

[57] ABSTRACT

16-dimethylaminomethylene-3-methoxy-1,3,5(10)-estratrien-17-one is a valuable new preparative intermediate which may be used, e.g., to prepare 17β-hydroxy-16β-ethyl-4-estren-3-one or 16β-ethylestradiol.

5 Claims, No Drawings

16-DIMETHYLAMINOMETHYLENE-3-METHOXY-1,3,5-(10)-ESTRATRIEN-17-ONE, A PROCESS FOR THE PREPARATION THEREOF AND ITS USE AS A PREPARATIVE INTERMEDIATE

BACKGROUND OF THE INVENTION

The present invention relates to a novel intermediate for the preparation of 16β-ethyl steroids of the estrane series having antiestrogenic and antiandrogenic activities, as well as a process for the preparation thereof.

It is known that 17β-hydroxy-16β-ethyl-4-estren-3-one is a medicinal agent effective for the treatment of benign hypertrophy of the prostate (G. Goto et al., Chem. Pharm. Bull. 26: 1718 [1978]). Furthermore, 16β-ethylestradiol seems promising for the treatment of hormone-dependent tumors. (M. K. Agarwal, Antihormones, Elsevier North-Holland, Amsterdam 1979, p. 307).

These compounds can be prepared in a 10-stage process from 3-methoxy-1,3,5(10)-estratrien-17-one as starting material. In this process, 3-methoxy-1,3,5(10)-estratrien-17-one is enolized and acylated with acetic anhydride. The thus-obtained $\Delta^{16}$-enol acetate is epoxidized with m-chloroperbenzoic acid and split in the presence of acetic acid. The resultant 16α-acetoxy-3-methoxy-1,3,5(10)-estratrien-17-one is saponified with sodium hydroxide solution in methanol and rearranged into 17β-hydroxy-3-methoxy-1,3,5(10)-estratrien-16-one. Subsequent Grignard reaction with ethylmagnesium iodide yields 3-methoxy-16,17β-dihydroxy-16α-ethyl-1,3,5(10)-estratriene, which is partially esterified with acetic anhydride/pyridine. The thus-obtained 3-methoxy-17β-acetoxy-16β-hydroxy-16α-ethyl-1,3,5(10)-estratriene is subjected to a Serini reaction with zinc/toulene and heating. The resultant 3-methoxy-16β-ethyl-1,3,5(10)-estratrien-17-one is reduced with sodium borohydride in ethanol. The ensuing 3-methoxy-16β-ethyl-1,3,5(10)-estratrien-17β-ol is reduced with lithium in liquid ammonia and then treated with hydrochloric acid/methanol, yielding the desired 17β-hydroxy-16β-ethyl-4-estren-3-one in a yield of barely 20% of theory.

This process has the obvious disadvantage that it requires a large number of stages and leads to relatively low yields due to the complicated synthetic path.

SUMMARY OF THE INVENTION

Accordingly, it is an object of the present invention to provide a process for preparing such 16β-ethyl steroids which involves fewer process stages and achieves higher yields of the desired final products.

Upon further study of the specification and appended claims, further objects and advantages of this invention will become apparent to those skilled in the art.

These objects have been attained by this invention by providing the novel intermediate compound 16-dimethylaminomethylene-3-methoxy-1,3,5(10)-estratrien-17-one from which 16β-ethyl steroids can be prepared in high yields.

DETAILED DISCUSSION

In order to prepare the compound of this invention, the same conventional starting material mentioned above, 3-methoxy-1,3,5(10)-estratrien-17-one is utilized. It is reacted with a derivative of N,N-dimethylformamide of the formula

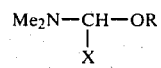

wherein X is Me$_2$N— or —OR, and
R is a lower alkyl residue of up to 5 carbon atoms, to obtain 16-dimethylaminomethylene-3-methoxy-1,3,5(10)-estratrien-17-one.

In this reaction, the N,N-dimethylformamide derivative is reacted with the 17-steroid ketone at temperatures above 100° C., e.g., 120°–150° C. Advantageously, the reaction is conducted without a solvent. However, it is also possible to effect the reaction in the presence of an inert, high-boiling solvent, e.g., toluene, xylene, decahydronaphthalene, silicone oil or diphenyl/diphenyl oxide. After cooling, the reaction product is worked up conventionally using, e.g., filtration, washing, recrystallization etc.

Also included within the scope of this invention as new intermediates are those substantial equivalents of 16-dimethyl-amino methylene-3-methoxy-1,3,5(10)-estratriene-17-one which may be used to prepare 16β-ethyl steroids, e.g., derivatives thereof substituted by alkyl groups (1-4 alkyl) at position C-7 (α or β) and hydroxyl group or ether and ester derivatives thereof at position C-1.

The novel intermediate of this invention can be utilized advantageously for the preparation of 16β-ethyl steroids such as the aforementioned compounds which, as is known, exhibit a high pharmacological efficacy.

For the preparation of 17β-hydroxy-16β-ethyl-4-estren-3-one and 16β-ethylestradiol, for example, 16-dimethylaminomethylene-3-methoxy-1,3,5(10)-estratrien-17-one can be subjected to a Grignard reaction with, e.g., methyllithium or methylmagnesium bromide under the usual conditions. (See, e.g., R. F. Abdulla et al., J. Org. Chem. 43: 4248 [1978]).

The thus-obtained 3-methoxy-16-ethylidene-1,3,5(10)-estratrien-17-one is then conventionally hydrogenated, e.g., in the presence of a noble metal catalyst, such as platinum or palladium, on a suitable support. (See, e.g. J. Fried and J. A. Edwards, Organic Reactions in Steroid Chemistry, Vol. I, Steroid Hydrogenation.)

The ensuing 3-methoxy-16β-ethyl-1,3,5(10)-estratrien-17-one can either be reacted with e.g. diisobutyl aluminium hydride, with ether cleavage and reduction, all of which reactions are conventional (see, e.g., G. Neef, U. Eder, G. Haffer, G. Sauer and R. Wiechert, Chem. Ber. 110, 3377 [1977]) in order to prepare the conventional antiestrogen 16β-ethyl-estradiol (16β-ethyl-1,3,5(10)-estratriene-3,17β-diol) or can be reacted in two stages to prepare the conventional antiandrogen 17β-hydroxy-16β-ethyl-4-estren-3-one, i.e., by reduction e.g. with a complex metal hydride, such as sodium borhydride or lithium aluminium hydride, to obtain first the corresponding 17β-alcohol (see, e.g., J. Fried and J. A. Edwards, Organic Reactions in Steroid Chemistry, Vol. I, Chapter 2, Reduction of Steroidal Ketones) followed by Birch reduction e.g. with an alkali metal in liquid ammonia. (See, e.g. ibid, Vol. I, Chapter 1, Reduction of Steroids by Metal-Ammonia Solutions).

The total yield for producing e.g., the antiandrogen is on the order of 70%; for producing the antiestrogen on the order of 80–85%.

While the foregoing reactions of the intermediate of this invention and substantial equivalents thereof have been written in terms of preparing two specific 16β-ethyl steroids, other 16β-steroids may be prepared therefrom by first reacting with a methyl-Grignard reagent as described above, followed by a sequence of reactions, the suitability of which can readily be determined by one skilled in the art employing conventional considerations for the desired 16β-ethyl steroid.

The following examples illustrate the advantageous uses of the novel intermediate.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples all temperatures are set forth uncorrected in degrees Celsius; unless otherwise indicated, all parts and percentages are by weight.

EXAMPLE 1

A mixture of 8.1 g. of 3-methoxy-1,3,5(10)-estratrien-17-one and 9.9 g. of bis(dimethylamino-tert.-butoxy)-methane is stirred for 60 minutes at 160° C. After cooling, the mixture is combined with ethanol and allowed to crystallize for 3 hours at −5° C. The crystallized product is removed by filtration, washed with ethanol, and recrystallized from ethanol, thus obtaining 10.2 g. of 16-dimethylaminomethylene-3-methoxy-1,3,5(10)-estratrien-17-one, m.p. 208°–210° C.

EXAMPLE 2

A solution of 5 g. of 16-dimethylaminomethylene-3-methoxy-1,3,5(10)-estratrien-17-one in 150 ml. of toluene is combined dropwise at −10° C. with 28.5 ml. of a 5% solution of methyllithium in ether. After this dropwise addition, the mixture is agitated for 15 minutes at −10° C.; then about 10 ml. of water is gently added in drops, and the reaction solution is poured into about 200 ml. of 0.5 N hydrochloric acid. The organic phase is separated, dried over sodium sulfate, and concentrated under vacuum. After crystallization of the residue from ethyl acetate/ether, 3.9 g. of 16-ethylidene-3-methoxy-1,3,5(10)-estratrien-17-one is obtained, m.p. 139°–140° C.

EXAMPLE 2

A suspension of 2.0 g. of 16-ethylidene-3-methoxy-1,3,5(10)-estratrien-17-one in 80 ml. of ethanol is combined with 200 mg. of 10% palladium-charcoal and hydrogenated for 60 minutes at room temperature under normal pressure. After removing the catalyst by filtration and concentration of the reaction product, 2.0 g. of 16β-ethyl-3-methoxy-1,3,5(10)-estratrien-17-one is obtained, m.p. 93°–94° C.

EXAMPLE 4

A solution of 6.4 g. of 16β-ethyl-3-methoxy-1,3,5(10)-estratrien-17-one in 100 ml. of 80% aqueous ethanol is combined at room temperature with 1.2 g. of sodium borohydride. The mixture is agitated for 2 hours at room temperature; then excess hydride is decomposed with 1 N hydrochloric acid, and the reaction solution is poured into about 200 ml. of water. The mixture is extracted with methylene chloride, dried over sodium sulfate, and concentrated. Recrystallization from ether yields 6.1 g. of 16β-ethyl-3-methoxy-1,3,5(10)-estratrien-17β-ol, m.p. 97°–99° C.

EXAMPLE 5

A solution of 2.0 g. of 16β-ethyl-3-methoxy-1,3,5(10)-estratrien-17β-ol in 40 ml. of tetrahydrofuran and 4 ml. of tert.-butanol is added dropwise at −40° C. to 80 ml. of ammonia. After the incremental introduction of 1.2 g. of lithium, the mixture is stirred for 2 hours at −40° C.; then the ammonia is allowed to evaporate, the residue is poured into about 200 ml. of water, and the mixture is extracted with ethyl acetate. The crude product is taken up in 40 ml. of methanol and 4 ml. of 4 N hydrochloric acid and agitated for 15 minutes at 50° C. Thereafter, the mixture is poured into water and extracted with methylene chloride. After recrystallizing the crude product from ethyl acetate/ether, 1.7 g. of 16β-ethyl-17β-hydroxy-4-estren-3-one is produced, m.p. 150°–152° C.

EXAMPLE 6

A solution of 2.0 g. of 16β-ethyl-3-methoxy-1,3,5(10)-estratrien-17-one in 40 ml. of toluene is combined at room temperature dropwise with 40 ml. of a solution of diisobutyl aluminum hydride (20%) in toluene; after this dropwise addition, the mixture is heated under reflux for 4 hours. After cooling, about 20 ml. of water is added dropwise to the solution at room temperature, the mixture is filtered over sodium sulfate, and the filtrate is concentrated. Crystallization of the residue from ethyl acetate yields 1.8 g. of 16β-ethyl-1,3,5(10)-estratriene-3,17β-diol, m.p. 171°–173° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a 16-ethylidene steroid which comprises reacting the corresponding 16-dimethylaminomethylene steroid with a methyl Grignard reagent.

2. A process for preparing 16β-ethyl-estradiol which comprises
   reacting 16-dimethylaminomethylene-3-methoxy-1,3,5(10)-estratrien-17-one with a methyl Grignard reagent, according to claim 1, thereby producing the corresponding 16-ethylidene derivative;
   hydrogenating the resultant 16-ethylidene derivative to produce the corresponding 16β-ethyl derivative; and
   ether cleaving and reducing the 16β-ethyl derivative to produce 16β-ethyl-estradiol.

3. A process for preparing 16β-ethyl-17β-hydroxy-4-estren-3-one which comprises
   reacting 16-dimethylaminomethylene-3-methoxy-1,3,5(10)-estratrien-17-one with a methyl Grignard reagent according to claim 1, thereby producing the corresponding 16-ethylidene derivative;
   hydrogenating the resultant 16-ethylidene derivative to produce the corresponding 16β-ethyl derivative;

reducing the 16β-ethyl derivative to produce the corresponding 17β-alcohol; and

Birch reducing the 17β-alcohol to produce 16β-ethyl-17β-hydroxy-4-estren-3-one.

4. A process for preparing a 16β-ethyl steroid which comprises reacting a 16-dimethylaminomethylene-steroid with a methyl Grignard reagent to produce the corresponding 16-ethylidene steroid according to claim 1, and hydrogenating the latter to produce the corresponding 16β-ethyl derivative.

5. A process of claim 1 comprising reacting 16-dimethylaminomethylene-3-methoxy-1,3,5(10)-estratrien-17-one with a methyl Grignard reagent thereby preparing the corresponding 16-ethylidene derivative.

* * * * *